US006818638B2

(12) United States Patent
Baenteli et al.

(10) Patent No.: US 6,818,638 B2
(45) Date of Patent: Nov. 16, 2004

(54) MELVINOLIN DERIVATIVES

(75) Inventors: Rolf Baenteli, Basel (CH); Wilfried Bauer, Lampenberg (CH); Sylvain Cottens, Witterswil (CH); Claus Ehrhardt, Loerrach (DE); Ulrich Hommel, Muellheim (DE); Jörg Kallen, Basel (CH); Josef Gottfried Meingassner, Perchtoldsdorf (AT); François Nuninger, Wittenheim (FR); Gabriele Weitz Schmidt, Bad Krozingen (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 10/192,888

(22) Filed: Jul. 11, 2002

(65) Prior Publication Data
US 2003/0087903 A1 May 8, 2003

Related U.S. Application Data

(63) Continuation of application No. 09/928,593, filed as application No. PCT/EP00/01191 on Feb. 14, 2000, now abandoned.

(30) Foreign Application Priority Data

Feb. 16, 1999 (GB) .............................. 9903546
Nov. 25, 1999 (GB) ............................. 9927880

(51) Int. Cl.$^7$ ...................... A61K 31/33; A61K 31/366; A61K 47/00; C07D 407/00; C07D 315/00
(52) U.S. Cl. ................... 514/183; 514/228.8; 514/315; 514/345; 514/529; 514/765; 514/769; 549/200; 549/263; 549/273; 549/293; 549/356; 549/425; 549/427; 549/426
(58) Field of Search ............................ 514/183, 228.8, 514/315, 345, 529, 765, 769; 549/200, 263, 273, 293, 356, 425, 426, 427

(56) References Cited

U.S. PATENT DOCUMENTS

| 5,021,451 | A | * | 6/1991 | McLane et al. ............. 514/460 |
| 5,393,893 | A |   | 2/1995 | Kubela et al. .............. 549/292 |
| 5,763,646 | A |   | 6/1998 | Kumar et al. ............... 560/252 |
| 5,763,653 | A |   | 6/1998 | Khanna et al. ............. 560/252 |

FOREIGN PATENT DOCUMENTS

| EP | 259 086 |   | 3/1988 |
| EP | 299 656 |   | 1/1989 |
| EP | 369263  | * | 5/1990 |
| EP | 0 415 488 |   | 3/1991 |
| EP | 605230  | * | 7/1994 |
| WO | WO 97/16184 |   | 5/1997 |
| WO | WO 98/32751 |   | 7/1998 |
| WO | WO 99/11258 |   | 3/1999 |

OTHER PUBLICATIONS

Chemical Abstract DN 114:221417, also cited as EP 369263.*
Norris DA.(PubMed Abstract 2258627, also cited as J. Invest. Dermatol., 95/6, 111–120(1990).*
Reinhardt et al(PubMed Abstract 12897816, also cited as Can J. Physiol. Pharmacol. 81/7, 690–5(2003).*
Menter et al(PubMed Abstract 12882019, also cited as Curr. Probl. Dermatol. 31, 50–63(2003).*
Schoenfeld et al(PubMed Abstract 12893080, also cited as Cancer Detect. Prev.,27/4,311–5(2003).*
Grau et al(PubMed Abstract 1679717, also cited as Eur. J. Immunol., 21/9,2265–7(1991).*
Wenke et al., "Simvastatin Reduces Graft Vessel Disease and Mortality After Heart Transplantation", Circulation, vol. 96, No. 5, pp. 1398–1402 (1997).
Niwa et al., "Inhibitory Effect of Fluvastatin, an HMG–CoA Reductase Inhibitor, on the Expression of Adhesion Molecules on Human Monocyte Cell Line.", Int. J. Immunopharmac., vol. 18, No. 11, pp. 669–675 (1996).
Di Napoli et al., "Does 3–Hydroxy–3–methylglutaryl Coenzyme A Reductase Inhibitor Therapy Exert a Direct Anti-Ischemic Effect!", Circulation, vol. 97, No. 9, p. 937 (1998).
Reichart et al., "What is the Role of Lipid Lowering Therapy in Heart–Allograft Failure!", Kidney International, vol. 48, Suppl. 52, pp. S52–S55 (1995).
Dustin et al., "Regulation of Locomotion and Cell–Cell Contact Area by the LFA–1 and ICAM–1 Adhesion Receptors", J. Immunol., vol. 148, No. 9, pp. 2654–2663 (1992).
Weitz–Schmidt et al., "An E–Selectin Binding Assay Based on a Polyacrylamide–Type Glycoconjugate", Anal. Biochem., vol. 238, pp. 184–190 (1996).
Derwent Abstracts, 98–414569/36 (AU 693401–B, Jan. 24, 1997).
Derwent Abstracts, 98–363269/31 (ZA 9704023, Mar. 13, 1997).
Derwent Abstracts, 98–121143/12 (AU 9721409, May 30, 1996).

* cited by examiner

Primary Examiner—Richard L. Raymond
Assistant Examiner—Sudhaker B. Patel
(74) Attorney, Agent, or Firm—Thomas R. Savitsky

(57) ABSTRACT

Mevinolin derivatives wherein the lactone ring is modified have interesting pharmaceutical properties, particularly in preventing or treating disorders or diseases mediated by LFA-1/ICAM-1 interactions.

12 Claims, No Drawings

MELVINOLIN DERIVATIVES

This application is a continuation of Application No. 09/928,593, filed Aug. 13, 2001 now abandoned which is a continuation of International Application No. PCT/EP00/01191, filed Feb. 14, 2000.

The present invention relates to mevinolin derivatives, a process for their production, their use as a pharmaceutical and pharmaceutical preparations containing them. More particularly the present invention provides a compound of formula I

I wherein
each of a - - - b and α - - - β independently, is either a single bond or a double bond;
$R_1$ is ········H,      ········$C_{1-4}$alkyl     or     ━━$OR_a$ wherein $R_a$ is H; $C_{1-6}$alkyl optionally substituted by OH or $C_{1-4}$alkoxy; $C_{2-6}$alkenyl; or aryl-$C_{1-4}$alkyl;

$R_2$ is OH; —O—CO—$R_5$ wherein $R_5$ is $C_{1-8}$alkyl, $C_{3-7}$cycloalkyl, $C_{3-7}$cycloalkyl-$C_{1-4}$alkyl, aryl or aryl-$C_{1-4}$alkyl; or —O—$R_6$ wherein $R_6$ is the residue of an α-amino-acid attached to O through its carbonyl residue or —CHR$_7$—COR$_5$ wherein $R_7$ is H, $C_{1-4}$alkyl, hetero $C_{1-4}$alkyl, $C_{3-7}$cycloalkyl, $C_{3-7}$cycloalkyl-$C_{1-4}$alkyl, aryl or aryl-$C_{1-4}$alkyl and $R_8$ is OH, $C_{1-4}$alkoxy or $NR_9R_{10}$ wherein each of $R_9$ and $R_{10}$ independently is H, $C_1$alkyl or $R_9$ and $R_{10}$ form together with the nitrogen to which they are bound, a heteroaryl group;

$R_3$ is a substituted lactam, piperidyl, linear amino alcohol or cyclic carbamate, or a residue of formula (i)

(i)

wherein
$R_{13}$ is OH; $C_{1-6}$alkoxy; —O—CO—$C_{1-6}$alkyl; or —O—CO—NHC$_1$alkyl;
$R_{14}$ is OH; $C_{1-4}$alkoxy; $C_{1-4}$alkyl; $C_{1-4}$alkoxy-carbonyl-$C_{1-4}$alkoxy; hydroxy-$C_{1-5}$alkoxy; $C_{1-4}$alkoxy-$C_{1-5}$alkoxy; $C_{1-4}$alkoxy-carbonyl-$C_{1-4}$alkyl; or $NR_{9a}R_{10a}$-$C_{1-5}$alkoxy wherein each of $R_{9a}$ and $R_{10a}$ independently has one of the significances given for $R_9$ and $R_{10}$;
$R_{15}$ is H or $C_{1-4}$alkyl; and
$R_{16}$ is $CONR_{17}R_{18}$ wherein one of $R_{17}$ and $R_{18}$ is H and the other is $C_{1-6}$alkyl, hydroxy-$C_{1-6}$alkyl, $C_{3-7}$cycloalkyl-$C_{1-4}$alkyl or aryl-$C_{1-4}$alkyl; or $C_{1-6}$alkoxy-carbonyl; each of a - - - b and α - - - β being a single bond when each of $R_{13}$ or $R_{14}$ is OH; and
$R_4$ is H or $OR_{19}$ wherein $R_{19}$ is $C_{1-6}$alkyl, hydroxy-$C_{1-6}$alkyl, $C_{1-4}$alkoxy-$C_{1-6}$alkyl, aryl-$C_{1-4}$alkyl or $C_{1-4}$alkoxycarbonyl-$C_{1-4}$alkyl, and wherever "aryl" appears as is or in the significances of "aryl-$C_{1-4}$alkyl" in the above definition, it is "phenyl" or "naphthyl" optionally substituted by halogen, OH, $NR_{11}R_{12}$, COOH, $CF_3$, $C_{1-4}$alkoxy, $C_{1-4}$alkyl, hydroxy-$C_{1-4}$alkyl, hydroxy-$C_1$alkoxy, $C_{1-4}$alkoxy-carbonyl, cyano or $CONR_{11}R_{12}$, each of $R_{11}$ and $R_{12}$ independently being H, $C_{1-4}$alkyl, phenyl, naphthyl, phenyl-$C_{1-4}$alkyl or naphthyl-$C_{1-4}$alkyl or $R_{11}$ and $R_{12}$ together with the nitrogen to which they are bound forming heteroaryl; and wherever "heteroaryl" appears, it is a 5- or 6-membered heterocyclic residue optionally fused to a benzene ring; in free form or in salt form.

Alkyl groups or alkyl moieties may be branched or straight chain. Cycloalkyl groups or moieties are preferably cyclopentyl or cyclohexyl. Heteroalkyl includes e.g. halogenated alkyl such as $CF_3$. Polyhydroxy-$C_{1-4}$alkyl may comprise up to 6 hydroxy groups.

Preferably the phenyl or naphthyl moiety in aryl or aryl-$C_{1-4}$alkyl, when substituted, bears up to 3 substituents as disclosed above, more preferably selected from $C_{1-4}$alkoxy, e.g. methoxy or ethoxy, hydroxy-$C_{1-4}$alkoxy, hydroxy-$C_{1-4}$alkyl and OH. When the phenyl moiety is disubstituted, the 2 substitutents are preferably in positions meta and para. Aryl-$C_{1-4}$alkyl is preferably benzyl, phenethyl or naphthyl-CH$_2$—, the phenyl or naphthyl moiety being optionally substituted as indicated above.

Examples of heteroaryl include pyrrolyl, imidazolyl, turyl, thienyl, pyrrolidinyl, piperidyl, piperazinyl, morpholino, pyridyl, indolyl or quinolyl. Heteroaryl as formed by $R_5$ and $R_{10}$ together with the nitrogen to which they are attached, may comprise a further heteroatom, e.g. O or N, and is preferably pyrrolidinyl, piperidyl, piperazinyl or morpholino. In heteroaryl-$C_{1-4}$alkyl, the alkyl moiety preferably is $C_1$ or $C_2$alkyl.

The significances given above for "aryl" and "heteroaryl" also applies to the radicals of formulae (a), (b), ($c_1$) or ($c_2$) hereinafter.

When $R_6$ is the residue of an α-amino acid, it may be the residue of a natural or unnatural α-amino acid residue, e.g. Ala, Leu, Ile, Val, Pro, wherein the terminal amino group may be substituted or unsubstituted, e.g. by an amino protecting group.

When $R_3$ is a substituted lactam residue, it is preferably a 6-membered ring wherein the nitrogen of the lactam may be substituted and/or comprising a further substituent on the ring, e.g. on the carbon atom opposite to the nitrogen. Preferably the lactam residue is disubstituted. A suitable example of a substituted lactam as $R_3$ includes e.g. a radical of formula (a)

(a)

wherein
$R_{30}$ is $C_{1-8}$alkyl; $C_{3-7}$cycloalkyl; aryl; $C_{3-7}$cycloalkyl-$C_{1-4}$alkyl; aryl-$C_{1-4}$alkyl; heteroaryl; or heteroaryl-$C_{1-4}$alkyl;

$R_{31}$ is OH; $C_{1-4}$alkoxy; $C_{1-4}$alkyl; $C_{1-4}$alkoxy-carbonyl-$C_{1-4}$alkoxy; hydroxy-$C_{1-5}$alkoxy; $C_{1-4}$alkoxy-$C_{1-5}$alkoxy; $C_{1-4}$alkoxy-carbonyl-$C_{1-4}$alkyl; amino-$C_{1-4}$alkoxy; HOOC—$C_{1-4}$alkoxy; HOOC—$C_{1-4}$alkyl; or $NR_{9a}R_{10a}$-$C_{1-5}$alkoxy wherein each of $R_{9a}$ and $R_{10a}$ independently has one of the significances given for $R_9$ and $R_{10}$.

When $R_3$ is a substituted piperidyl residue, the nitrogen of the piperidyl may be substituted and/or a further substituent may be present on the ring, e.g. on the carbon atom opposite to the nitrogen. Preferably the piperidyl residue is disubstituted. A suitable example of a substituted piperidyl residue includes e.g. a radical of formula (b)

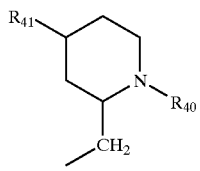

(b)

wherein $R_{40}$ has one of the significances given for $R_{30}$; and $R_{41}$ has one of the significances given for $R_{31}$ or is —O—CO—$C_{1-8}$alkyl.

When $R_3$ is a substituted amino alcohol residue, the amino group thereof may be monosubstituted, e.g. by a substituent such as aryl-$C_{1-4}$alkyl or aryl-$C_{1-4}$alkyl-carbonyl, and/or a further substituent may be present on the chain, e.g. on the carbon atom adjacent to the alcohol or amino group. Cyclisation of the substituted amino alcohol residue leads to a corresponding substituted cyclic carbamate. A suitable example of a substituted amino alcohol and of the corresponding substituted cyclic carbamate includes e.g. a radical of formula ($c_1$) or ($c_2$)

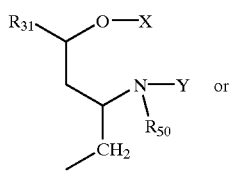

($c_1$)

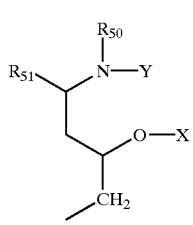

($c_2$)

wherein either each of X and Y is H or X and Y form together

, each of $R_{50}$, independently is H; $C_{1-8}$alkyl; $C_{3-7}$cycloalkyl; aryl; $C_{3-7}$cycloalkyl-$C_{1-4}$alkyl; aryl-$C_{1-4}$alkyl; heteroaryl; heteroaryl-$C_{1-4}$alkyl; $C_{1-4}$alkylcarbonyl; aryl-carbonyl; heteroaryl-carbonyl; aryl-$C_{1-4}$alkyl-carbonyl or heteroaryl-$C_{1-4}$alkyl-carbonyl, and each of $R_{51}$, independently is H; $C_{1-4}$alkyl; hydroxy-$C_{1-4}$alkyl; amino-$C_{1-4}$alkyl; $C_{1-4}$alkoxy-$C_{1-4}$alkyl; $C_{1-4}$alkoxy-carbonyl-$C_{1-4}$alkyl wherein $C_{1-4}$alkoxy is optionally substituted by amino, $C_{1-4}$alkyl-amino or di-($C_{1-4}$alkyl)amino; HOOC—$C_{1-4}$alkyl; or $R_{23}R_{24}N$—CO—$C_{1-4}$alkyl wherein $R_{23}$ is H, $C_{1-4}$alkyl, hydroxy-$C_{1-4}$alkyl, polyhydroxy-$C_{1-8}$alkyl, heteroaryl, heteroaryl-$C_{1-4}$alkyl, amino-$C_{1-4}$alkyl, $C_{1-4}$alkylamino-$C_{1-4}$alkyl, di-($C_{1-4}$alkyl)amino-$C_{1-4}$alkyl or aryl-$C_{1-4}$alkyl and $R_{24}$ is H, $C_{1-4}$alkyl or hydroxy-$C_{1-4}$alkyl, at least one of $R_{50}$ and $R_{51}$ being other than H.

Preferred compounds of formula I are those wherein $R_3$ is substituted lactam, substituted linear amino alcohol, substituted cyclic carbamate, preferably substituted lactam or substituted cyclic carbamate, e.g. as disclosed above, more preferably a radical of formula (a) or ($c_1$) or ($c_2$) wherein X and Y are —CO—.

In the compounds of formula I, the following significances are preferred individually or in any sub-combination:

1. $R_1$ is H or $CH_3$, preferably $CH_3$;
2. $R_2$ is —O—CO—$R_5$, preferably wherein $R_5$ is $C_4$alkyl, particularly —CH($CH_3$)—$CH_2$—$CH_3$, —CH($CH_2$—$CH_2$—$CH_3$)$_2$, —CH($CH_2$—$CH_3$)$_2$, —C($CH_3$)$_2$—$CH_2$—$CH_3$ —$CH_2$—$CH_3$)—$CH_2$—$CH_2$—$CH_3$.
3. a - - - b is a double bond;
4. α - - - β is a double bond;
5. $R_4$ is H;
6. $R_3$ is a radical of formula (i);
7. $R_{16}$ is CO—$NR_{17}R_{18}$; preferably one of $R_{17}$ and $R_{18}$ is H;
8. Each of $R_{13}$ and $R_{1-4}$ is OH and each of a - - - b and α - - - β is a single bond;
9. Each of $R_{13}$ and $R_{1-4}$ is other than OH;
10. $R_3$ is a radical of formula (a);
11. $R_{30}$ in (a) is aryl-$C_{1-4}$alkyl or heteroaryl-$C_{1-4}$alkyl, preferably benzyl or naphthyl-methyl wherein the phenyl or naphthyl ring is optionally substituted by OH, $C_{1-4}$alkoxy, hydroxy-$C_{1-4}$alkoxy or hydroxy-$C_{1-4}$alkyl, or morpholino, pyridyl, indolyl or quinolyl;
12. $R_{31}$ in (a) is OH, $C_{1-4}$alkoxy, hydroxy-$C_{1-4}$alkoxy, $C_{1-4}$alkoxy-carbonyl-$C_{1-4}$alkoxy or HOOC—$C_{1-4}$alkoxy;
13. $R_3$ is a radical of formula ($c_1$) or ($c_2$) wherein X and Y form together —CO—;
14. $R_{50}$ in ($c_1$) or ($c_2$) wherein X and Y form together —CO—, is aryl-$C_{1-4}$alkyl or heteroaryl-$C_{1-4}$alkyl, preferably benzyl or naphthyl-methyl wherein the phenyl or naphthyl ring is optionally substituted by OH, $C_1$alkoxy, hydroxy-$C_{1-4}$alkoxy or hydroxy-$C_1$alkyl;
15. $R_{51}$ in ($c_1$) or ($c_2$) wherein X and Y form together —CO—, is hydroxy-$C_{1-4}$alkyl; amino-$C_{1-4}$alkyl; $C_{1-4}$alkoxy-$C_{1-4}$alkyl; $C_{1-4}$alkoxycarbonyl-$C_{1-4}$alkyl; HOOC—$C_{1-4}$alkyl; or $R_{23}R_{24}N$—CO—$C_{1-4}$alkyl.

Compounds of formula I may exist in free form or in salt form, e.g. as acid addition salts with e.g. organic or inorganic acids, for example, hydrochlorides, or salts when a COOH is present, as salts with bases e.g. alkali salts such as sodium or potassium, or substituted or unsubstituted ammonium salts.

It will be appreciated that the radicals of formulae (i), (a), (b), (c₁) and (c₂) may comprise at least one asymetric carbon atom, e.g. the carbon atom which bears $R_{15}$ and $R_{16}$, $R_{31}$, $R_{41}$ or $R_{51}$, respectively, for example

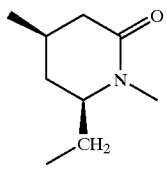

(a')

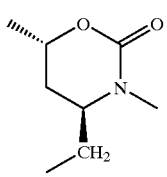

(c₁')

Where the stereochemistry of any part of a compound of the invention is not specified, it is to be understood that the present invention embraces individual enantiomers and their mixtures. Similar considerations apply in relation to starting materials exhibiting asymmetric carbon atoms as mentioned above. Where compounds of the invention exist in isomeric form as aforementioned, individual isomers may be obtained in conventional manner, e.g. employing optically active starting materials or by separation of initially obtained mixtures, for example using conventional chromatographic techniques.

The present invention also includes a process for the production of a compound of formula I, comprising a) for the production of a compound of formula I wherein $R_3$ is a residue of formula (i) submitting mevinolin or compactin or the corresponding tetrahydro-mevinolin or -compactin to ring opening, e.g. by reaction with a corresponding amine, e.g. arylamine; or b) for the production of a compound of formula I wherein 3 is a radical of formula (c₁) wherein each of X and Y is H, submitting to reductive amination the carbonyl function in $R''_3$ in a compound of formula IV

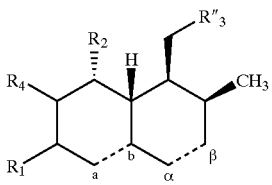

(IV)

wherein $R_1$, $R_2$, $R_4$, a - - - b and α - - - β and $R_1$ are as defined above, and $R''_3$ is a radical of formula ($c_{1A}$)

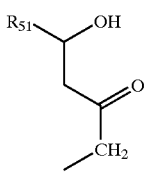

($c_{1A}$)

wherein $R_{51}$ is as defined above; or c) for the production of a compound of formula I wherein $R_3$ is a residue of formula (c₂) wherein each of X and Y is H, submitting mevinolin or compactin wherein the lactone ring has been converted into a conjugated ad unsaturated lactone, to a 1,4-addition e.g. with an amine, e.g. veratrylamine, and concomitant ring opening with an alcohol, e.g. methanol; or d) for the production of a compound of formula I wherein $R_3$ is a residue of formula (c₁) or (c₂) wherein each of X and Y is —CO—, submitting to cyclisation a compound of formula I wherein $R_3$ is a residue of formula (c₁) or (c₂) wherein each of X and Y is H; or e) for the production of a compound of formula I wherein $R_3$ is a substituted lactam, e.g. a residue of formula (a), submitting a compound of formula I wherein $R_3$ is a residue of formula (i) wherein $R_{13}$ is OH oxidised to a ketone and $R_{16}$ is $CONHR_{18}$, to a reductive amination and concomitant ring closure; or converting the free OH group in $R_3$ in a compound of formula I wherein $R_3$ is a residue of formula (i) wherein $R_{16}$ is $CONHR_{18}$, into a leaving group, e.g. by mesylation, and then submitting the resulting compound to a basic treatment; or f) for the production of a compound of formula I wherein $R_3$ is a substituted piperidyl, e.g. a residue of formula (b), reducing a compound of formula I wherein $R_3$ is a substituted lactam, e.g. a residue of formula (a);

and, where required, removing the protecting group where present, and converting the resulting compound of formula I in free form or in salt form.

Where OH groups are present in the starting products which are not to participate in the reaction, they may be protected, in accordance with known methods. OH protecting groups are known in the art, e.g. tert.-butyl-dimethyl-silanyl.

Process steps (a) to (f) may be effected analogously to methods known in the art or as disclosed in the Examples below. The cyclisation in step (d) may conveniently be carried out in the presence of a cyclisation agent, e.g. carbonyl diimidazole.

Compounds of formula IV may be prepared by opening of the OH protected lactone ring according to known procedures, e.g. by reaction with an amine and then oxidation of the resulting hydroxy group into a ketone. Insofar as the production of the starting materials is not particularly described, the compounds are known or may be prepared analogously t methods known in the art or as disclosed in WO 99/11258, e.g. starting from mevinolin or compactin or tetrahydro-mevinolin or -compactin. The —O—CO—CH (CH₃)—C₂H₅ of mevinolin, compactin or tetrahydro-mevinolin or -compactin may also be reduced to OH and then esterified to another —O—CO—R₅ group.

The following Examples are illustrative of the invention. Following abbreviations are used:

Boc=tert.-butoxy-carbonyl
rt=room temperature
OMe=methoxy
THF=tetrahydrofurane
DMF=dimethylformamide
DCC=N,N'-dicyclohexylcarbodiimide
Pro=proline
TBDMS=tert-butyldimethylsilyl
DMAP=dimethylaminopyridine
CDI=carbonyldiimidazole
TBME=tert-butylmethylether
CHX=cydohexane

EXAMPLE 1

(S)-2-Methyl-butyric acid (S)-(3R,7S,8aR)-8-{(S)-2-[(4R,6R)-3(4-hydroxy-3-methoxy-benzyl)-4-[(2-hydroxy-ethylcarbamoyl)methyl]-2-oxo[1,3]oxazinan-6-yl]ethyl}-3,7dimethyl-1,2,3,7,8,8a-hexahydro-naphthalen-1-yl ester

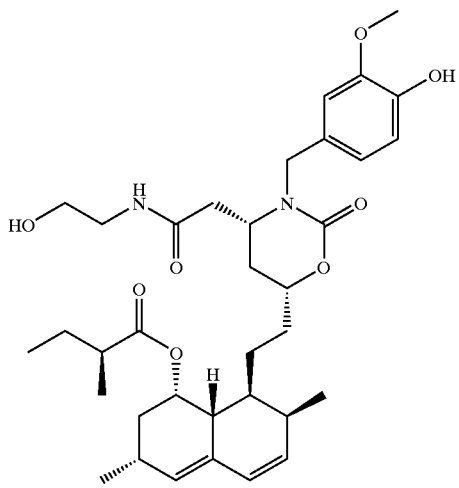

a) To a solution of 40.4 g mevinolin ((S)-2-Methyl-butyric acid (1S,3R,7S,8S,8aR)-8-[2-((1R,3R)-4-hydroxy-6-oxo-tetrahydro-pyran-2-yl)-ethyl]-3,7dimethyl-1,2,3,7,8,8a-hexahydro-naphthalen-1-yl ester) in 100 ml of CH$_2$Cl$_2$ are added 24.4 g DMAP, then slowly 15.0 g Ac$_2$O. The mixture is stirred overnight at rt. The reaction is controlled by TLC, TBME/CHX, 3:2. The reaction mixture is diluted with TBME, washed successively with water, ca. 15% citric acid, brine, then dried over sodium sulfate. The organic phase is concentrated and the product cristallized by addition of diisopropylether. The precipitate is filtred, washed with diisopropylether and dried, yielding the α,β unsaturated lactone derivative (S)-2-methyl-butyric acid (S)-(3R,7S,8aR)-7-methyl-3-methyl-8-[(S)-2-((R)-6-oxo-3,6dihydro-2H-pyran-2-yl)-ethyl]—1,2,3,7,8,8a-hexahydro-naphthalen-1-yl ester.

MS (FAB-MS), 387 (MH+)

b) To 15.5 g of compound a) in 250 ml MeOH is added 14.4 g of the 4-(tert-butyl-dimethyl-silanyloxy)-3-methoxy-benzylamine and the mixture is stirred overnight. TLC control in TBME. The reaction mixture is completely evaporated and the crude product separated by flash-chromatography on silica gel (CHX→TBME→MeOH). The desired methylester (S)-2-methyl-butyric acid (S)-(3R,7S,8aR)-8-{(R(3R,5R)-5-[4-(tert-butyl-dimethyl-silanyloxy)-3-methoxy-benzylamino]-3-hydroxy-6methylcarbamoyl-hexyl}-7-methyl-3-methyl-1,2,3,7,8,8a-hexahydro-naphthalen-1-yl ester is obtained.

MS, (ESI), 686.5 (MH+)

c) A solution of 12.5 g of the compound as obtained in b), in 25 ml DMF is treated with 4.1 g CDI and stirred for ca. 5 h. at rt. TLC control in TBME/ CHX, 3:2. The reaction mixture is diluted with TBME, extracted with water and then brine, the organic phase dried over sodium sulfate and evaporated. The crude product is purified by RP-18 chromatography, MeOH/H2O→MeOH. After rechromatography on silica gel, TBME/CHX→TBME, the cyclic carbamate (S)-2-Methyl-butyric acid (S)-(3R,7S,8aR)-8-((S)-2-((4R,6R)-3-[4-(tert-butyl-dimethyl-silanyloxy)-3-methoxy-benzyl]-4-methylcarbamoylmethyl-2oxo-[1,3]oxazinan-6-yl)-ethyl)-7-methyl-3-methyl-1,2,3,7,8,8a-hexahydro-naphthalen-1-yl ester is obtained as a foam.

MS (ESI), 712.5 (MH+)

d) To a solution of 6.0 g of the compound as obtained in c) in 25 ml MeOH is added a total of 5.5 g 2-amino-ethanol and the mixture is heated at reflux, for ca. 40 hrs., until completion (TLC control in moist ethyl acetate). The reaction mixture is diluted with ethyl acetate, extracted with citric acide and brine, then dried over sodium sulfate and evaporated. The crude product is purified as above, first by RP-18 chromatography then on silica gel. The title product is obtained as a white foam.

MS (ESI): 627.4 (MH+)

EXAMPLE 2

(S)2-Methyl-butyric acid (S)-3R,7S,8aR)-8-{(S)-2-[(4R,6R)3-(4-hydroxy3-methoxy-benzyl)-4-methylcarbamoylmethyl-2-oxo-[1,3]oxazinan-6yl]-ethyl}-7-methyl-3-methyl-1,2,3,7,8,8a-hexahydro-naphthalen-1-yl ester

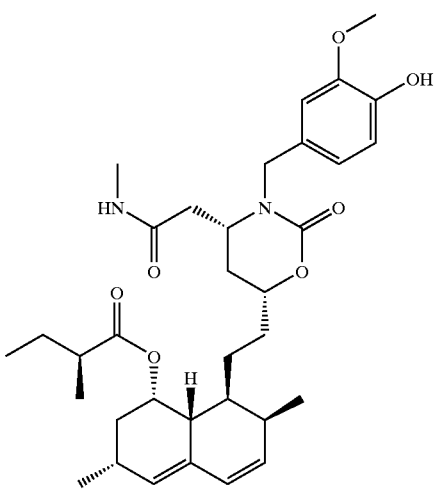

3.6 g of the compound as obtained in Example 1c) is dissolved in 100 ml of a solution of ca. 30% methylamine in MeOH and stirred at rt for ca. 24 hrs. (TLC control in moist ethyl acetate). The reaction mixture is evaporated and the crude product purified by silica gel chromatography (TMBE/CHX ->ethyl acetate). Pure fractions are combined, evaporated and the title compound is obtained as a foam.

(ESI): 597.4 (MH+) $[\alpha]^{20}_D$=+234.7° (c=1 in methanol)

By following the same procedure, but using the appropriate starting material, the diastereomer wherein the carbamate ring has the configuration

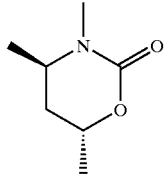

is also obtained.

By following the procedure as disclosed in Examples 1 and 2, the compounds of formula X

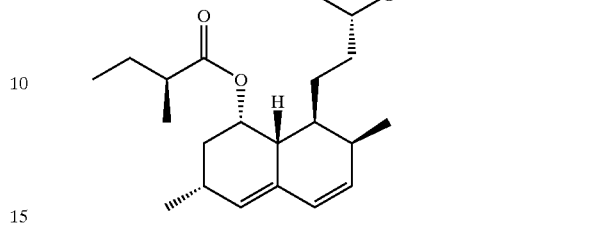

wherein $R_{50}$ and $R_{51}$ are as defined in Table 1 below, may be prepared.

TABLE 1

| EX | $R_{50}$ | $R_{51}$ | M.S. (ESI) |
|---|---|---|---|
| 3* | 3-OMe-4-OH-benzyl | —CH$_2$—CO—NH—CH$_2$—(4'-OH-3'-OMe-phenyl) | 717 [M − H] |
| 4 | 3-OMe-4-(2-hydroxy-ethoxy)-benzyl | —CH$_2$—CO—NH—CH$_2$—[3'-OMe-4'-(β-hydroxy-ethoxy)-phenyl] | 851 [M + HCOO—] |
| 5 | 3,4-di-OMe-benzyl | —CH$_2$—CO—NHCH$_3$ | 611 [MH+] |
| 6 | 3,4-di-OMe-benzyl | —CH$_2$—COOH | 596 [M − H] |
| 7 | 3-OMe-4-OH-benzyl | —CH$_2$—CO—OCH$_3$ | 596 [M − H] |
| 8 | 3-OMe-4-OH-benzyl | —CH$_2$—COOH | 582 [M − H] |
| 9 | 3-OMe-4-OH-benzyl | —CH$_2$—CO—N(CH$_3$)$_2$ | 609 [M − H] |
| 10 | 3-OMe-4-OH-benzyl | —CH$_2$—CH$_2$—OH | 570 [MH+] |
| 11 | 3,4-di-OH-benzyl | —CH$_2$—CO—NH—CH$_2$-(3',4'-di-OH-phenyl) | 689 [M − H] |
| 12 | 3,4-di-OMe-benzyl | —CH$_2$—CO—N—CH(CH$_2$OH)$_2$ | 669 [M − H] |
| 13 | 3-OMe-4-(2-hydroxy-ethoxy)-benzyl | —CH$_2$—CO—NHCH$_3$ | 639 [M − H] |
| 14 | 3-OMe-4-OH-benzyl | —CH$_2$—CO—NH—CH$_2$—CH(OH)—CH$_2$OH | 655 [M − H] |
| 15 | 3,4-di-OH-benzyl | —CH$_2$—CO—OCH$_3$ | 582 [M − H] |
| 16 | 3,4-di-OH-benzyl | —CH$_2$—CO—NHCH$_2$CH$_2$OH | 611 [M − H] |
| 17 | 3-OMe-4-OH-benzyl | —CH$_2$—CO—NH—CH(CH$_2$—OH)$_2$ | 655 [M − H] |
| 18 | 3,4-di-OMe-benzyl | —CH$_2$—CO—NH—CH$_2$—CH$_2$OH | 640 [M − H] |
| 19 | 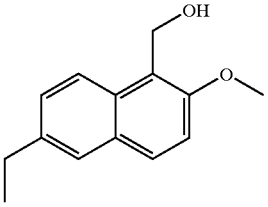 | —CH$_2$—CO—NH—CH$_2$—CH$_2$OH | 689 [M − H] |
| 20 | 3-OMe-4-OH-benzyl | —CH$_2$—CO—NH—CH$_2$—(CHOH)$_4$—CH$_2$OH | 745 [M − H] |
| 21 | 3-OMe-4-OH-benzyl | —CH$_2$—CO—N—(CH$_2$CH$_2$OH)$_2$ | 669 [M − H] |
| 22 | 3-OMe-4-OH-benzyl | —CH$_2$—CO—NH—(CH$_2$)$_2$—N(CH$_3$)$_2$ | 654 [MH+] |
| 23 | 4-OMe-3-OH-benzyl | —CH$_2$—CO—NH—CH$_2$—CH$_2$OH | 671 [M + HCOO—] |
| 24 | 3,4-di-OMe-benzyl | —CH$_2$—CO—NH-(3,4-di-OMe-benzyl) | 721 [MH+] |

*The diastereoisomer of the compound of Ex. 3, wherein the cyclic carbamate residue has the configuration

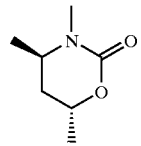

is also prepared by following the same procedure.

By following the procedure below the compounds of formula $X_1$ may be prepared. The OH protected lactone ring of mevinolin or compactin may also be submitted to ring opening, e.g. by reaction with an amine, then treatment of the resulting hydroxyamine with carbonyl-diimodazole leads to the carbamate.

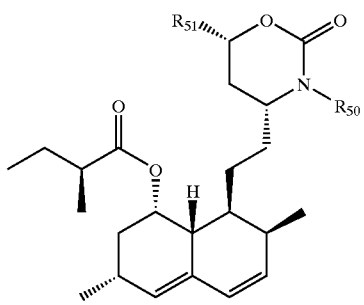
$X_1$ wherein $R_{50}$, $R_{51}$ are as defined in Table 2 below.

TABLE 2

| Ex | $R_{50}$ | $R_{51}$ | M.S. (ESI) |
|---|---|---|---|
| 25* | 3,4-di-OMe-benzyl | —CH$_2$—CO—NHCH$_3$ | 611 (M + H) |
| 26 | 3,4-di-OMe-benzyl | —CH$_2$—CO—O—(CH$_2$)$_2$—N(CH$_3$)$_2$ | 668 (M + H) |

*The diasteromer of the compound of Ex. 25, wherein the cyclic carbamate residue has the configuration

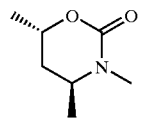

is also prepared by following the same procedure.

EXAMPLE 27

(S)-2-Methyl-butyric acid (S)-3S,4aS,7S,5S,8S,8aS)-8-{(S)-2-[(4R,6R)-3-(4-hydroxy-3-methoxy-benzyl)-4-[(2-hydroxy-ethylcarbamoyl)-methyl]-2-oxo-[1,3]oxazinan-6-yl]-ethyl}-3,7-dimethyldecahydro-naphthalen-1-yl ester By following the first step of the procedure to prepare example 28 (to obtain trans tetrahydro mevinolin) and then the procedure (step a) to d) as disclosed in Example 1, the compound of formula

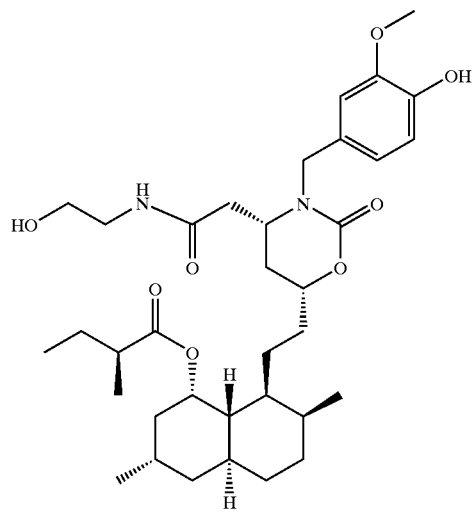

is obtained. MS (ESI): 629 [M-H].

EXAMPLE 28

(S)-2-Methyl-butyric acid (S)-(3S,4aS,7S,8S,8aS)-8-[(3R,5)6-(3,4-dimethoxy-benzylcarbamoyl)-3,5-dihydroxy-hexyl]-3,7-dimethyl-decahydro-naphthalen-1-yl ester

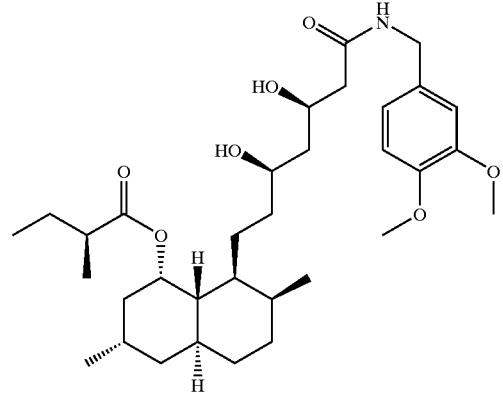

a) To a solution of 40 g (0.098 mol) of mevinolin in 31 ethyl acetate is added 10 g Pt/Al2O3. The mixture is hydrognated under an H$_2$ atmosphere under 2.6 bar pressure for 16 h. The mixture is filtered and the solvent evaporated. The residue is purified by silical gel chromatography using ethyl acetate/cyclohexane 8/2 as a solvent. First eluted is the undesired cis isomer, followed by a side product with one double bond. Finally the desired trans isomer is eluted. Several crystallizations yielded the desired trans tetrahydro-mevinolin ((S)2-Methylbutyric acid (S)-(3S,4aS,7S,5S,8S,8aS)-8-[2-((2R,4R)-4-hydroxy-6-oxotetrahydro-pyran-2-yl)-ethyl]3-methyl-7-methyl-decahydro-naphthalen-1-yl ester).

b) To a solution of 2 g (5.0 mmol) of the trans tetrahydro mevinolin obtained in a) in 12 ml ethanol is added 3.7 ml (25.0 mmol) 3,4-dimethoybenzylamine. The reaction mixture is stirred for 20 h at rt, then it is diluted with 300 ml diethyl ether with and washed with 100 ml of water. The organic extract is dried with $MgSO_4$ and evaporated. The residue is purified by chromatography on silicagel using ethyl acetate as eluent to give the title compound.

MS (ESI): 598 (M+Na), 574 (M-H)

The compound of Example 29 is obtained by silylating mevinolin, following step b) of the procedure of Example 28, reacting with ethyl isocyanate and desilylating according to conventional methods. The compound of example 30 is obtained by reacting mevinolin with ethyl diazoacetate and rhodium acetate and then following step b) of the procedure of Example 28.

The compound of Example 31 is prepared by following step a) and b) of the procedure of Example 1 and desilylating the compound resulting from step b). The compounds of Examples 32 and 33 are obtained by submitting the appropriate starting materials to step a) and a modified version of step b) (in the absence of methanol):

EXAMPLE 29

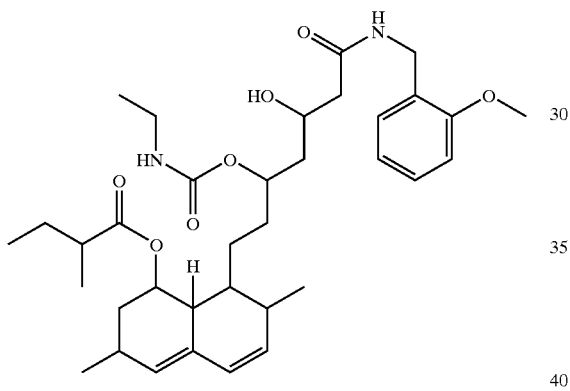

MS(ESI): 613 (M+H)

EXAMPLE 30

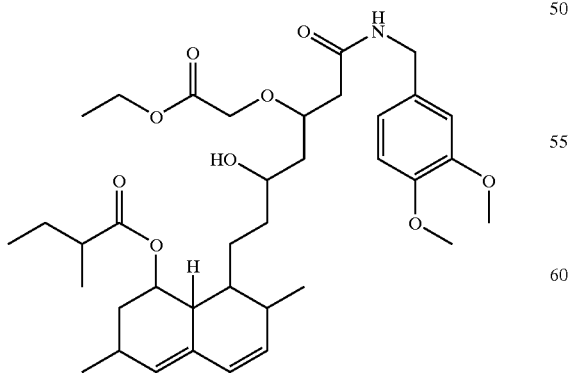

MS(ESI): 658 (M+H)

EXAMPLE 31

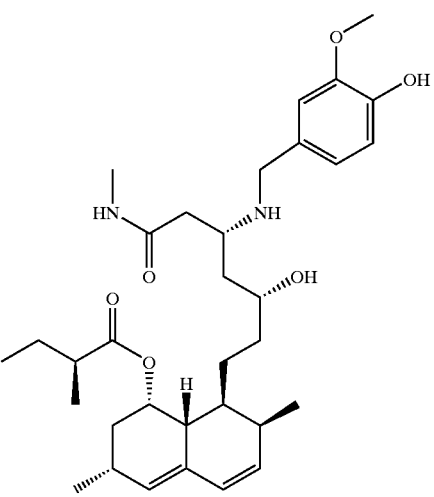

MS (ESI): 571 [MH+]

EXAMPLES 32 and 33

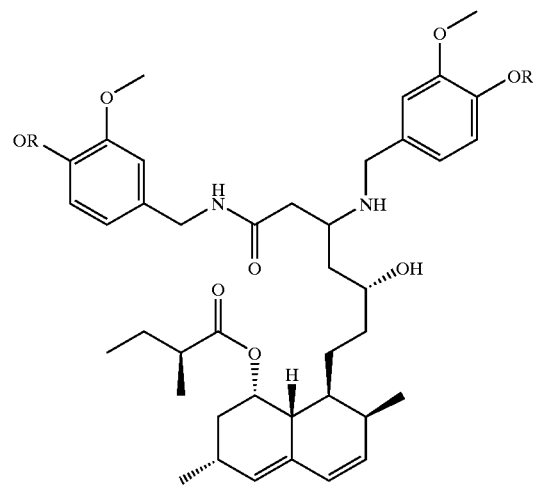

Ex. 32 R = H  MS (ESI): 693 [MH+]
Ex. 33 R = $CH_3$  MS (ESI): 791 [M+HCOO]

EXAMPLE 34

(S)2-Methyl-butyric acid (1S,3R,7S,8S,8aR)-8-{2-[(2S, 4R)4-hydroxy-1-(5-hydroxymethyl-6-methoxy-naphthalen-2-ylmethyl)-6-oxo-piperidin-2-yl]-ethyl}-3,7-dimethyl-1,2,3,7,8,8a-hexahydro-naphthalen-1-yl ester

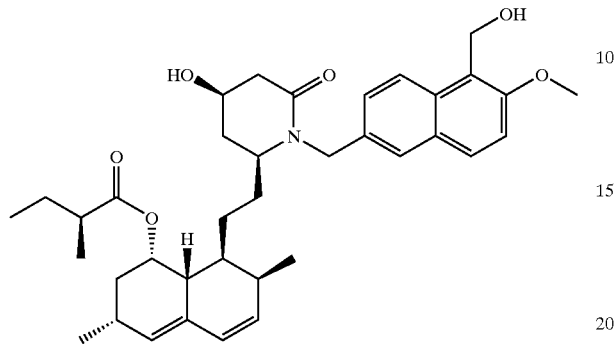

a) To a stirred solution of 22 g (37 mmol) of silylated mevinolin (obtained by standard silylation of mevinolin in the 4 position) ((S)-2-Methyl-butyric acid (3R, 7S,8S,8aR)-8-{2-[(2R,4R)4-(tert-butyldimethyl-silanyloxy6-oxo-tetrahydropyran-2-yl]-ethyl}-3,7-dimethyl-1,2,3,7,8,8a-hexahydro-naphthalen-1-yl ester) in 65 ml THF at rt are added 18 g (56 mmol) of C-[5-(tert-butyl-dimethyl-silanyloxymethyl)-6-methoxy-naphthalen-2-yl]-methylamine (prepared from 2-bromo-6-methoxy-naphthalene). After 18 hours the reaction mixture is diluted with 250 ml methyl-t-butyl ether and washed successively with 10% aqueous citric acid, saturated aqueous sodium bicarbonate and brine. The organic phase is dried over sodium sulfate and the solvent evaporated. The crude product is purified by silica gel chromatography (hexane/ethyl acetate 4/1 to 3/2) to afford the hydroxyamide 2-methyl-butyric acid 8-(5-(tert-butyl-dimethyl-silanyloxy)-6-{[5-(tert-butyl-dimethyl-silanyloxymethyl)-6-methoxy-naphthalen-2-ylmethyl]-carbamoyl}-3-hydroxy-hexyl)-3,7-dimethyl-1,2,3,7,8,8a-hexahydro-naphthalen-1-yl ester as a white foam.

MS (ESI, −Q1MS) 894.6; 884.3; 848.5 b) To a stirred, cooled (0° C.) solution of 4.3 g (5.0 mmol) of the compound obtained under 34a) above and 1.4 ml (10 mmol) trethylamine in 40 ml THF are added 0.51 ml (6.6 mmol) of methanesulfonyl chloride. After 30 minutes 6.5 ml (13 mmol) of a 2M solution of sodium bis(trimethylsilyl)amide in THF are added. The mixture is stirred for 1 hour at 0° C. the reaction is quenched with 10% aqueous citric acid and diluted with methyl-t-butyl ether. The phases are separated and the aqueous phase is extracted twice with methyl-t-butyl ether. The organic phases are combined, washed successively with saturated aqueous sodium bicarbonate and brine, dried over sodium sulfate and the solvent is evaporated. The crude product is purified by silica gel chromatography (hexane/ethyl acetate 95/5 to 4/1) to afford the lactam 2-methyl-butyric acid 8-(2-{4-(tert-butyl-dimethyl-silanyloxy)-1-[5-(tert-butyldimethyl-silanyloxymethyl)-6-methoxy-naphthalen-2-ylmethyl]-6-oxo-piperidin-2-yl}-ethyl)-3,7dimethyl-1,2,3,7,8,8a-hexahydro-naphthalen-1-yl ester as a white foam.

MS (ESI, +Q1MS) 832.6; 598.4 c) To a stirred solution of 106 mg (0.13 mmol) of the compound obtained under 34b) above in 2 ml THF at room temperature are added 606 µl (0.62 mmol) of a 1N aqueous HCl solution. After 18 hours the reaction is quenched with saturated aqueous sodium bicarbonate and diluted with methyl-t-butyl ether. The phases are separated and the aqueous phase is extracted twice with methyl-t-butyl ether. The combined organic phases are washed with brine, dried over sodium sulfate and the solvent is evaporated. The crude product is purified by silica gel chromatography (hexane:ethyl acetate 1:1 to 1:4) to afford the pure title compound as a white foam.

MS (ESI, −Q1MS) 648.4; 602.5 $[\alpha]^{20}_D$+119.3° (c=1 in methanol) m.p.≈145° C.

The compounds of formula $X_2$

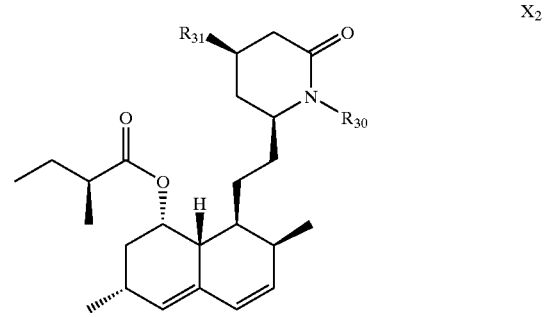

wherein $R_{30}$ and $R_{31}$ have the significances given in Table 3, are prepared analogously to procedure as disclosed in Example 34.

TABLE 3

| Ex | $R_{30}$ | $R_{31}$ | M.S |
|---|---|---|---|
| 35 | ![quinoline-ethyl] | OH | 545 [MH+] |
| 36* | ![quinoline-ethyl] | OH | 545 [MH+] |
| 37 | 4-(2'-OH-ethoxy)-3-OCH₃-benzyl | OH | 628 [M + HCOO—] |

TABLE 3-continued

| Ex | R₃₀ | R₃₁ | M.S |
|---|---|---|---|
| 38 | 3,5-di-(OCH₃)-benzyl | OH | 554 [MH+] |
| 39 | 3,4-di-(OCH₂CH₃)-phenyl | OH | 568 [MH+] |
| 40 | β-naphthyl-CH₂— | OH | 544 [MH+] |
| 41 | 4-di-ethyl-carbamoyl-benzyl | OH | 593 [MH+] |
| 42 | 3-OCH₃-4-OH-benzyl | OH | 538 [M − H] |
| 43 | 4-morpholinocarbonyl-benzyl | OH | 607 [MH+] |
| 44 | (6-ethyl-2-methoxy-naphthyl) | OH | 619 [M + HCOO—] |
| 45 | 4-ethoxy-carbonyl-benzyl | OH | 566 [MH+] |
| 46* | (5-methyl-1H-indol-3-yl) | OH | 519 [MH+] |
| 47** | (3,4-dimethoxy)-benzyl | OH | 554 [M + H] |
| 48 | 4-pyridyl-CH₂— | OH | 495 (M + H) |
| 49** | 3-pyridyl-CH₂— | OH | 494 (M) (EI) |
| 50 | CH₃ | OH | 418 (M + H) |
| 51 | 3-benzoxy-benzyl | OH | 600 (M + H) |
| 52* | 3-benzoxy-benzyl | OH | 600 (M + H) |
| 53 | 3-isopropoxy-benzyl | OH | 596 (M + HCOO) |
| 54* | 3-isopropoxy-benzyl | OH | 552 (M + H) |
| 55 | (3,4-dimethoxy)-phenethyl | OH | 568 (M + H) |
| 56 | p-CF₃-benzyl | OH | 562 (M + H) |
| 57 | p-tert.-butoxy-benzyl | OH | 594 (M + H) |
| 58 | (6-ethyl-2-methoxy-naphthyl-CH₂OH) | OCH₃ | 640 [MNa+] |
| 59** | m-methoxy-benzyl | OH | 523 (M) (EI) |
| 60* | benzyl | OCH₃ | 508 (M + H) |
| 61 | 3-OCH₃-4-(2'-OH-ethoxy)-benzyl | O—CH₂—CO—OC₂H₅ | 715 [M + HCOO—] |
| 62 | 3-OCH₃-4-(2'-OH-ethoxy)-benzyl | O—CH₂—CH₂—OH | 628 [MH+] |
| 63* | benzyl | OCH₂CH₂OH | 538 (M + H) |
| 64* | benzyl | O—CH₂—COOH | 552 (M + H) |

*In these compounds the lactam moiety has the following configuration:

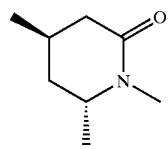

**Both diastereoisomers are obtained and each can be isolated.

The synthesis of compounds of Examples 61 to 64* additionally comprise a treatment with ethyl diazoacetate and rhodium acetate, followed for the compounds of Examples 62* and 63*, by a reduction.

By following the procedure of Example 34 but using as starting material the corresponding tetrahydro-mevinolin derivative and 3,4-dimethoxy-benzylamine, the following compound is obtained:

EXAMPLE 65

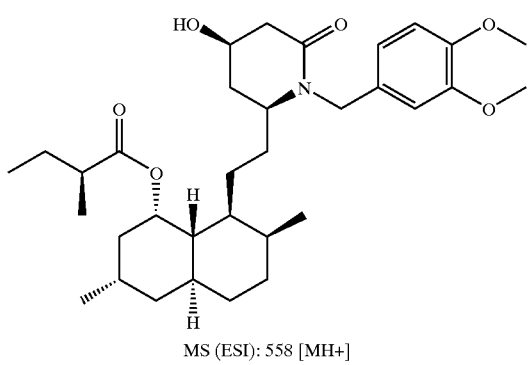

MS (ESI): 558 [MH+]

Compounds of Ex. 66 and 67 may be obtained from mevinolin as follows: ester cleavage of mevinolin and oxidation of the newly generated hydroxy position to the oxo compound. The neighbouring hydroxy substituent is then introduced via the formation of the silylenolate and treatment with meta-chloroperbenzoic acid. Selective alkylation of the newly formed hydroxy position is achieved by treatment with Meerwein salt. The ester group is introduced via its anhydride. Then the procedure as described for Ex. 34 is followed.

EXAMPLE 66

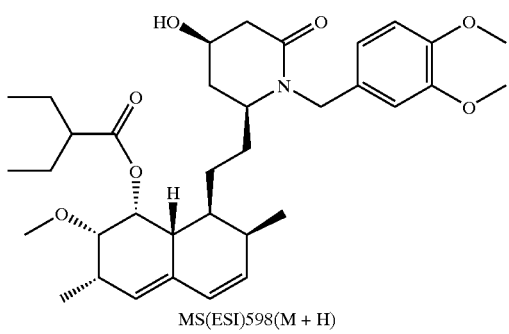

MS(ESI)598(M + H)

EXAMPLE 67

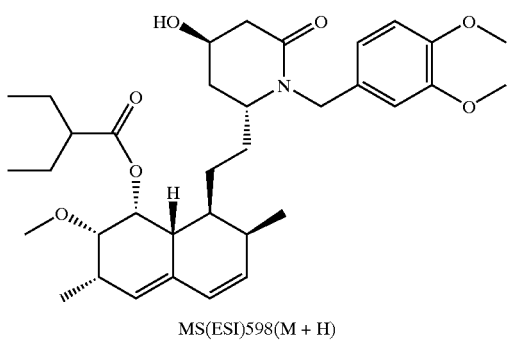

MS(ESI)598(M + H)

EXAMPLE 68

(S)-2-Methyl-butyric acid (1S,3R,7S,8S,8aR)—O—[2-((R)-1-benzyl-4-methyl-6-oxo-piperidin-2-yl)-ethyl]3,7-dimethyl-1,2,3,7,8,8a-hexahydro-naphthalen-1-yl ester Mevinolin is treated with acetic anhydride to give the α,β-unsaturated lactone. This is treated with cuprous bromide dimethylsulfide complex and methyl lithium to affect conjugate addition. The methylated lactone compound is treated with methanol and diazabicycloundecane to give the ring opened methylated hydroxy ester. The hydroxy group of which is then oxidized with sulfur trioxide pyridine complex to the corresponding ketone.

The ketone is reductively aminated (as described for Example 76b) to give the title compound MS(EI): 491 (M)

By following the procedure of Example 68, but using the appropriate starting materials, the compounds of formula $X_3$

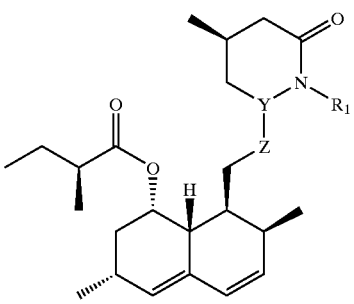

$X_3$ wherein $R_1$ and Y-Z are as defined in Table 4 below, may be prepared:

TABLE 4

| Example | Y—Z | $R_1$ | MS (EI) |
|---|---|---|---|
| 68 | C—C | —CH$_2$—phenyl | see above |
| 69 | C⃤C | —CH$_2$—CH(CH$_3$)$_2$ | 457 (M) |
| 70 | C⃥C | —CH$_2$—CH(CH$_3$)$_2$ | 457 (M) |

EXAMPLE 71

(S)-2-Methylbutyric acid (1S,3R,7S,8S,8aR)-8-{2-[(2S,4S)1-(3,4-dimethoxy-benzyl)-4-hydroxy-6oxo-piperidin-2-yl]ethyl}-3,7dimethyl-1,2,3,7,8,8a-hexahydronaphthalen-1-yl ester a) To a solution of 600 mg (1.1 mmol) of 2-methyl-butyric acid 8-(2-[1-(3,4-dimethyoxy-benzyl)-4-hydroxy-6-oxopiperidin-2-yl]-ethyl)-3,7-dimethyl-1,2,3,7,8,8a-hexahydro-naphthalen-1-yl ester in 15 ml of THF at rt are added 2 ml of a 65% RedAl® solution in toluene. After 3 hours, the reaction is quenched by the addition of 1 ml of methanol. The organic phase is extracted twice with 15 ml of 2N HCl. The aqueous phases are combined, brought to pH 12 with 1N NaOH and extracted three times with ethyl acetate. The organic phases are combined, dried over sodium sulfate and the solvent evaporated. The residue is purified by silica gel chromatography (t-butyl methyl ether/methanol 9/1) to afford pure 1-(3,4-Dimethoxy-benzyl)-2-[2-(8-hydroxy-2,6-dimethyl-1,2,6,7,8,8a-hexahydro-naphthalen-1-yl)-ethyl]-piperidin-4-ol as a white foam. MS (ESI) 456 (M+H)

b) The above compound is treated with diethylacetic anhydride in the presence of catalytic amounts of 4-dimethylaminopyridine in dichloromethane at rt for 16 h to give a diacylated compound. The undesired acyl group on the lactone moiety is cleaved by transesterification with methanol at 55° C. for 5 h to give the title compound.

MS (ESI): 554 (M+H). See formula below in Table 5.

By following the procedure of Example 71, but using the appropriate starting materials, the compounds of formula $X_4$

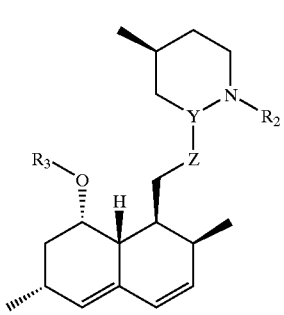

wherein $R_1$-$R_3$ and Y-Z are as defined in Table 5 below, may be prepared reaction mixture is stirred for 3 hours at rt. It is then diluted with 30 ml of ethyl acetate and washed successively with a saturated aqueous sodium bicarbonate solution and water. The organic phase is dried over sodium sulfate and the solvent evaporated. The residue is crystallized from diethyl ether to afford the desired product 2-methyl-butyric acid 8-(5-hydroxy-6-methylcarbamoyl-3-oxo-hexyl)-3,7-dimethyl-1,2,3,7,8,8a-hexahydro-naphthalen-1-yl ester as white crystals.

MS (FAB) 440 (M+Ll)

b) To a solution of 300 mg (0.69 mmol) of the compound of formula 76a) in 2 ml of dichloroethane are added 200 mg (1.2 mmol) of veratrylamine, 244 mg (1.15 mmol) of sodium triacetoxyborohydride and 60 mg (1.0 mmol) of acetic acid. The reaction mixture is stirred overnight at room temperature. It is then diluted with 20 ml of ethyl acetate and washed successively with a saturated aqueous sodium bicarbonate solution, water and brine. The organic phase is dried over sodium sulfate and the solvent evaporated. The residue is purified by silica gel chromatography (tert.-butyl methyl ether/methanol/$NH_4OH_{aq}$ 90/9/1) to afford the title compound as a white foam.

MS (ESI) 585 (M+H)

TABLE 5

| Ex | $R_1$ | $R_2$ | $R_3$ | Y—Z | MS (ESI) |
|----|-------|-------|-------|-----|----------|
| 71 | OH | 3,4-dimethoxy-benzyl | ($CH_3$—$CH_2$)$_2$CH—CO— | C◄═C | see above |
| 72 | OH | 3,4-dimethoxy-benzyl | ($CH_3$—$CH_2$)$_2$CH—CO— | C·····C | 554 (M + H) |
| 73 | ($CH_3$—$CH_2$)$_2$CH—CO—O— | 3,4-dimethoxy-benzyl | ($CH_3$—$CH_2$)$_2$CH—CO— | C◄═C | 674 (M + Na) |
| 74 | ($CH_3$—$CH_2$)$_2$CH—CO—O— | 3,4-dimethoxy-benzyl | ($CH_3$—$CH_2$)$_2$CH—CO— | C·····C | 652 (M + H) |
| 75 | ($CH_3$—$CH_2$)$_2$CH—CO—O— | 3,4-dimethoxy-benzyl | H | C·····C | 554 (M + H) |

Compound of Ex. 73 is obtained from compound of Ex. 71 starting from compound of Ex. 47. Compound of Ex. 74 is obtained from compound of Ex. 72 starting from the diastereoisomer of Ex. 50**.

EXAMPLE 76

(S)-2-Methyl-butyric acid (1S,3R,7S,8S,8aR)-8-[(3R,5R)3-(3,4-dimethoxy-benzylamino)-5-hydroxy-6-methylcarbamoyl-hexyl]-3,7-dimethyl-1,2,3,7,8,8a-hexahydronaphthalen-1-yl ester a) To a solution of 900 mg (1.65 mmol) of 2-methyl-butyric acid 8-[5-(tert.-butyl-dimethyl-silanyloxy)-6-methylcarbamoyl-3oxo-hexyl]-3,7-dimethyl-1,2,3,7,8,8a-hexahydro-naphthalen-1-yl ester in 5 ml of THF are added 700 mg (11.7 mmol) of acetic acid and 1.0 g (3.2 mmol) of tetrabutylammonium fluoride trihydrate. The By following the procedure of Example 76, but using the appropriate starting materials, the compounds of formula $X_5$

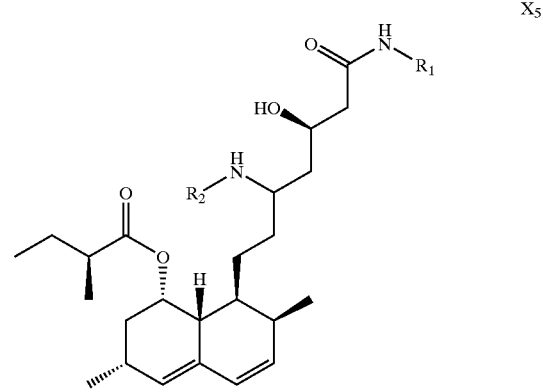

wherein $R_1$ and $R_2$ are as defined in Table 6 below, may be prepared.

TABLE 6

| Ex | $R_1$ | $R_2$ | MS (ESI) |
|---|---|---|---|
| 76 | $CH_3$ | -(3,4-dimethoxy)-benzyl | see above |
| 77 | $CH_3$ | benzyl | 525 (M + H) |
| 78 | $CH_3$ | diphenyl-methyl | 601 (M + H) |
| 79 | $CH_3$ | $CH(CH_3)$-phenyl | 539 (M + H) |

The compounds of formula I, in free form or in pharmaceutically acceptable salt form exhibit valuable pharmacological properties, e.g. inhibiting activity of LFA-1/IACAM-1 or ICAM-3 interactions or inhibiting inflammation, e.g. as indicated in in vitro and in vivo tests and are therefore indicated for therapy.

A. In vitro:

i. Cell Free Assay

The assay measures the binding of soluble human ICAM-1 to Immobilized human LFA-1 is purified from JY cells, a human lymphoblastoid B cell-line, by immunoaffinity chromatography as described by Dustin et al. (J. Immunol. 148, 2654–2663, 1992). ICAM-1 mouse $C_\kappa$ fusion protein (ICAM-1) is produced using the baculovirus system as described by Weitz-Schmidt et al. (Anal. Biochem.238, 184–190, 1996).

Purified LFA-1 is diluted 1:20 in phosphate buffered saline (PBS) containing 2 mM $MgCl_2$, pH 7.4 and coated onto microtitre plates (Nunc) at 37° C. for 3h. Plates are blocked with 1% heat-treated BSA in PBS for 2 hours at 37° C. followed by a washing step using PBS, 2 mM $MgCl_2$, 1% fetal calf serum, pH 7.4 (assay buffer). Compounds dissolved at 10 mM in DMSO are diluted in assay buffer and added to the plates. Biotinylated recombinant ICAM-1 in assay buffer (6 μg/ml) is added and allowed to bind at 37° C. for one hour. After incubation, wells are washed with assay buffer. Streptavidin-peroxidase diluted 1:5000 in assay buffer is added and incubated for 45 min at 37° C. Plates are then washed with assay buffer and 2.2'-azino-bis(3-ethylbenzothiazoline-6 sulfonic acid) diammonium salt substrate solution is added to each well. The reaction is stopped after 20 min and bound ICAM-1 is determined by measuring the optical density at 405 nm in a microplate reader.

In this assay, compounds of formula I inhibit adhesion of LFA-1 to ICAM-1 with an $IC_{50} \leq 30$ μM, preferably 0.05 to 30 μM.

ii) Human Mixed Lymphocyte Reaction (MLR)

Peripheral blood mononuclear cells (PBMC) are isolated from human buffy coats. In each experiment, PBMC from three different donors (A, B, and C) are set up in three individual 2-way reactions (A-B, A-C, B-C). Cells are cocultured for six days and proliferation is determined by pulsing the cells with $^3$H-thymidine. The concentration of compounds of formula I which results in 50% inhibition of cell proliferation ($IC_{50}$) is calculated. In this assay, compounds of formula I inhibit the MLR with an $IC_{50}$ in the range of 0.2 to 4 μM.

B. In vivo i) Murine Thioglycollate Induced Peritonitis

Thioglycollate is injected I.p. to mice and immediately thereafter the compound to be tested is given s.c. The mice are killed after 4 hours, the peritoneal cavity lavaged and total number of neutrophils in the lavage fluid is determined. In this assay, the compounds of formula I inhibit thioglycollate induced neutrophil migration when administered s.c. at a dose of from 0.001–50 μg/kg.

ii) Allergic Contact Dermatitis (ACD)

Groups of oxazolone-sensitized mice are challenged with 10 μl of 0.2 or 2.0% oxazolone on the inner surface of the right to eliciate ACD. The low concentration of oxazolone is used for testing compounds on systemic activity whereas the high concentration is applied for topical testing. The unchallenged left ears serve as normal controls and dermatitis is evaluated from the individual differences in pinnal weight, which is taken as a measure of increase in inflammatory swelling 24 h after the challenge. Dermatitis is evaluated in test- and for comparison in control groups. The test groups are treated with the test compounds either orally (twice, 2 h and immediately before challenge), subcutaneously (immediately before challenge) or topically (30 min after challenge at the site of elicitation of the ACD); the controls are treated similarly with the vehicles alone. For oral and subcutaneous administration the compounds are administered in an oil in water emulsion, for topical administration the compounds are prepared in a mixture of ethanol, acetone and dimethylacetamide. The data of the test- and the vehicle-treated control groups are statistically analysed by ANOVA followed by Dunnet T-test (normal distribution or data) or by H and U-test, respectively. When administered p.o. at a dose of from 0.1 to 10 mg/kg, compounds of formula I inhibit the elicitation phase of allergic contact dermatitis.

iii) Transplantation: Heterotopic mouse heart allograft

The strain combination used: BALB/c=>$C_3$H (H-2d=>H-2k) comprises MHC and non-MHC mismatch. Female animals are anaesthetised using inhalational isofluorane. Following heparinisation of the donor BALB/c mouse through the abdominal inferior vena cava with simultaneous exsanguination via the aorta, the chest is opened and the heart rapidly cooled. The aorta is ligated and divided distal to the first branch and the brachiocephalic trunk is divided at the first bifurcation. The left pulmonary artery is ligated and divided and the right side divided but left open. All other vessels are dissected free, ligated and divided and the donor heart is removed into iced saline.

The recipient $C_3$H is prepared by dissection and cross-clamping of the infra-renal abdominal aorta and vena cava. The graft is implanted with end-to-side anastomoses, using 11/0 monofilament suture, between the donor brachiocephalic trunk and the recipient aorta and the donor right pulmonary artery to the recipient vena cava. The clamps are removed, the graft tethered retroabdominally, the abdominal contents washed with warm saline and the animal is closed and allowed to recover under a heating lamp. Graft survival is monitored by daily palpation of the beating donor heart through the abdominal wall. Rejection is considered to be complete when heart beat stops. Improvements of graft function are obtained in animals treated with a compound of formula I administered orally at a daily dose of 30 mg/kg. Significant improvement is obtained when the compound of formula I is administered with an immunosuppressive agent, e.g. cyclosporin A, at a daily dose of 10 mg/kg.

The compounds of formula I are, therefore, useful in the treatment and/or prevention of diseases or disorders mediated by LFA-1/ICAM-1 or ICAM-3 Interactions e.g. ischemia/reperfusion injury e.g. myocardial infarction, stroke, gut ischemia, renal failure or hemorrhage shock, acute or chronic rejection of organ or tissue allo- or xenografts, e.g. heart, lung, combined heart-lung, kidney, liver, bowel, bone marrow or pancreatic islets, infection diseases such as septic shock, adult respiratory distress syndrome, or traumatic shock. The compounds of formula I are also useful in the treatment and/or prevention of acute or chronic inflammatory diseases or disorders or autoimmune diseases e.g. rheumatoid arthritis, systemic lupus erythematosus, hashimoto's thyroidis, multiple sclerosis, myasthenia gravis, diabetes type I and uveitis, cutaneous manifestations of immunologically-mediated illnesses, inflammatory and hyperproliferative skin diseases (such as psoriasis, atopic dermatitis, alopecia aerata, allergic contact dermatitis, irritant contact dermatitis and further eczematous dermatitises, seborrhoeic dermatitis, lichen planus, pemphigus, bullous pemphigoid, epidermolysis bullosa, urticaria, angloedemas, vasculitides, erythema multiforme, cutaneous eosinophilias, lupus erythematosus, acne, granuloma annulare, pyoderma gangrenosum, sun burns or toxic epidermal necrolysis), inflammatory bowel disease, ophthalmic inflammatory diseases or immune-mediated conditions of the eye, such as auto-immune diseases, e.g. keratoplasty and chronic keratitis, allergic conditions, e.g. vernal conjunctivitis, inflammatory conditions and corneal transplants. Compounds of formula I are useful as immunosuppressive agents.

For the above uses the required dosage will of course vary depending on the mode of administration, the particular condition to be treated and the effect desired. In general, satisfactory results are indicated to be obtained systemically at daily dosages of from about 0.1 to about 10 mg/kg body weight. An indicated daily dosage in the larger mammal is in the range from about 0.5 mg to about 80 mg, conveniently administered, for example, in divided doses up to four times a day or in retard form.

For topical use satisfactory results are obtained with local administration of a 1–3% concentration of active substance several times daily, e.g. 2 to 5 times daily.

The compounds of formula I may be administered systemically or topically, by any conventional route, in particular enterally, e.g. orally, e.g. in the form of tablets or capsules, topically, e.g. in the form of lotions, gels, ointments or creams, or in a nasal or a suppository form. Percutaneous administration via patches or other delivery systems may also be a possible route for prevention or treatment of above diseases.

Pharmaceutical compositions comprising a compound of formula I in association with at least one pharmaceutical acceptable carrier or diluent may be manufactured in conventional manner by mixing with a pharmaceutically acceptable carrier or diluent. Unit dosage forms contain, for example, from about 0.1 mg to about 40 mg of active substance.

Topical administration is e.g. to the skin. A further form of topical administration is to the eye.

The compounds of formula I may be administered in free form or in pharmaceutically acceptable salt form e.g. as indicated above. Such salts may be prepared in conventional manner and exhibit the same order of activity as the free compounds.

In accordance with the foregoing the present invention further provides:

1.1 A method for preventing or treating disorders or diseases mediated by LFA-1/ICAM-1 interactions, e.g. such as Indicated above, in a subject in need of such treatment, which method comprises administering to said subject an effective amount of a compound of formula I or a pharmaceutically acceptable salt thereof;

1.2 A method for preventing or treating acute or chronic inflammatory diseases or disorders or autoimmune diseases, e.g. as indicated above, in a subject in need of such treatment, which method comprises administering to said subject an effective amount of a compound of formula I or a pharmaceutically acceptable salt thereof;

2. A compound of formula I, in free form or in a pharmaceutically acceptable salt form for use as a pharmaceutical, e.g. in any of the methods as indicated under 1.1 and 1.2 above.

3. A pharmaceutical composition for use in any of the methods as in 1.1 and 1.2 above comprising a compound of formula I in free form or pharmaceutically acceptable salt form in association with a pharmaceutically acceptable diluent or carrier therefor.

4. A compound of formula I or a pharmaceutically acceptable salt thereof for use in the preparation of a pharmaceutical composition for use in any of the method as in 1.1 and 1.2 above.

The compounds of formula I may be administered as the sole active ingredient or in conjunction with, e.g. as an adjuvant to, other drugs in immunomodulating regimens or other anti-inflammatory agents for the treatment or prevention of allo- or xenograft acute or chronic rejection or inflammatory or autoimmune disorders. For example, the compounds of formula I may be used in combination with cyclosporins, rapamycins or ascomycins, or their immunosuppressive analogs, e.g. cyclosporin A, cyclosporin G, FK-506, ABT-281, ASM981, rapamycin, 40-O-(2-hydroxy) ethyl-rapamycin etc.; corticosteroids; cyclophosphamide; azathioprene; methotrexate; FTY720; leflunomide; mizoribine; mycophenolic add; mycophenolate mofetil; 15-deoxyspergualine; immunosuppressive monoclonal antibodies, e.g., monoclonal antibodies to leukocyte receptors, e.g., MHC, CD2, CD3, CD4, CD7, CD25, CD28, B7, CD40, CD45 or CD58 or their ligands; or other immunomodulatory compounds, e.g. CTLA4Ig, or other adhesion molecule inhibitors, e.g. mAbs or low molecular weight inhibitors including Selectin antagonists and VLA-4 antagonists. A preferred composition is with Cyclosporin A, FK506, rapamycin or 40-(2-hydroxy)ethyl-rapamycin.

Where the compounds of formula I are administered in conjunction with other immunosuppressive/immunomodulatory or anti-inflammatory therapy, e.g. for preventing or treating chronic rejection as hereinabove specified, dosages of the co-administered immunosuppressant, immunomodulatory or anti-inflammatory compound will of course vary depending on the type of co-drug employed, e.g. whether it is a steroid or a cyclosporin, on the specific drug employed, on the condition being treated and so forth. In accordance with the foregoing the present invention provides in a yet further aspect:

5. A method as defined above comprising co-administration, e.g. concomitantly or in sequence, of a therapeutically effective amount of a compound of formula I in free form or in pharmaceutically acceptable salt form, and a second drug substance, said second drug substance being an immunosuppressant, immunomodulatory or anti-inflammatory drug, e.g. as indicated above.

6. A therapeutic combination, e.g. a kit, for use in any method as defined under 1.1 or 1.2 above, comprising a compound of formula I, in free form or in pharmaceutically acceptable salt form, with at least one pharmaceutical composition comprising an immunosuppressant, immunomodulatory oranti-inflammatory drug. The kit may comprise instructions for its administration.

Compounds of Examples 2, 28 and 34 are preferred, particularly for use in the treatment of inflammatory skin diseases, e.g. as indicated above. In one test run, following results were obtained: an $IC_{50}$ of 0.05, 0.79 and 0.19 $\mu M$, respectively for the compounds of Ex. 2, 28 and 34, in the test Ai); an $IC_{50}$ of 0.2 $\mu M$ for the compound of Ex. 2 in the MLR test Aii); an $ED_{50}$ of 0.1 $\mu g/kg$ p.o. for the compound of Ex. 2 in the test Bi); in Bii) compound of Ex. 2 has an inhibiting effect of 41% when administered p.o. at a dose of 2×3 mg/kg and compound of Ex. 34 inhibits inflammatory swelling by 41% at 2x 1 mg/kg p.o.

Preferred compounds of formula I are those inhibiting HMG CoA Reductase activity with an $IC_{50} \geq 1$ μM, e.g. 24 50 μM, in the in vitro Microsomal assay as disclosed in WO 99/11258.

What is claimed is:

1. A compound of formula I

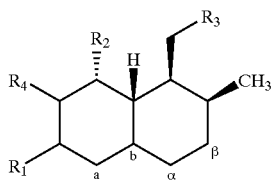

I wherein each of a - - - b and α - - - β independently, is either a single bond or a double bond;

$R_1$ is

⋯H, ⋯$C_{1-4}$alkyl or —$OR_a$ wherein $R_a$ is H, $C_{1-6}$alkyl optionally substituted by OH or $C_{1-4}$alkoxy, $C_{2-6}$alkenyl or aryl-$C_{1-4}$alkyl;

$R_2$ is OH; —O—CO—$R_5$ wherein $R_5$ is $C_{1-8}$alkyl, $C_{3-7}$cycloalkyl, $C_{3-7}$cycloalkyl-$C_{1-4}$alkyl, aryl or aryl-$C_{1-4}$alkyl; or —O—$R_6$ wherein $R_6$ is the residue of an α-amino-acid attached to O through its carbonyl residue or —$CHR_7$—$COR_8$ wherein $R_7$ is H, $C_{1-4}$alkyl, hetero$C_{1-4}$alkyl, $C_{3-7}$cycloalkyl, $C_{3-7}$cycloalkyl-$C_{1-4}$alkyl, aryl or aryl-$C_{1-4}$alkyl and $R_6$ is OH, $C_{1-4}$alkoxy or $NR_9R_{10}$ wherein each of $R_9$ and $R_{10}$ independently is H, $C_{1-4}$alkyl or $R_9$ and $R_{10}$ form together with the nitrogen to which they are bound, a heteroaryl group;

$R_3$ is a substituted linear amino alcohol or cyclic carbamate of formula $(c_2)$;

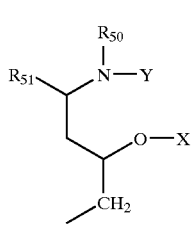

($c_2$)

wherein each of $R_{50}$, independently is H; $C_{1-8}$alkyl; $C_{3-7}$cycloalkyl; aryl; $C_{3-7}$cycloalkyl-$C_{1-4}$alkyl; aryl-$C_{1-4}$alkyl; heteroaryl; heteroaryl-$C_{1-4}$alkyl; $C_{1-4}$alkylcarbonyl; aryl-carbonyl; heteroaryl-carbonyl; aryl-$C_{1-4}$alkyl-carbonyl or heteroaryl-$C_{1-4}$alkyl-carbonyl, and each of $R_{51}$, independently is H; $C_{1-4}$alkyl; hydroxy-$C_{1-4}$alkyl; amino-$C_{1-4}$alkyl; $C_{1-4}$alkoxy-$C_{1-4}$alkyl; $C_{1-4}$alkoxy-carbonyl-$C_{1-4}$alkyl wherein $C_{1-4}$alkoxy is optionally substituted by amino, $C_{1-4}$alkyl-amino or di-($C_{1-4}$alkyl)amino; HOOC—$C_{1-4}$alkyl; or $R_{23}R_{24}N$—CO—$C_{1-4}$alkyl wherein $R_{23}$ is H, $C_{1-4}$alkyl, hydroxy-$C_{1-4}$alkyl, polyhydroxy-$C_{1-8}$alkyl, heteroaryl, heteroaryl-$C_{1-4}$alkyl, amino-$C_{1-4}$alkyl, $C_{1-4}$alkylamino-$C_{1-4}$alkyl, di-($C_{1-4}$alkyl)amino-$C_{1-4}$alkyl or aryl-$C_{1-4}$alkyl and $R_{24}$ is H, $C_{1-4}$alkyl or hydroxy-$C_{1-4}$alkyl, at least one of $R_{50}$ and $R_{51}$ being other than H, each of X and Y is H or X and Y form together each of a - - - b and α - - - β being a single bond when each of $R_{13}$ or $R_{14}$ is OH; and

, $R_4$ is H or $OR_{19}$ wherein $R_{19}$ is $C_{1-6}$alkyl, hydroxy-$C_{1-6}$alkyl, $C_{1-4}$alkoxy-$C_{1-6}$alkyl, aryl-$C_{1-4}$alkyl or $C_{1-4}$alkoxycarbonyl-$C_{1-4}$alkyl, and wherever "aryl" appears as is or in the significances of "aryl-$C_{1-4}$alkyl" in the above definition, it is "phenyl" or "naphthyl" optionally substituted by halogen, OH, $NR_{11}R_{12}$, COOH, $CF_3$, $C_{1-4}$alkoxy, $C_{1-4}$alkyl, hydroxy-$C_{1-4}$alkyl, hydroxy-$C_{1-4}$alkoxy, $C_{1-4}$alkoxy-carbonyl, cyano or $CONR_{11}R_{12}$, each of $R_{11}$ and $R_{12}$ independently being H, $C_{1-4}$alkyl, phenyl, naphthyl, phenyl-$C_{1-4}$alkyl or naphthyl-$C_{1-4}$alkyl or $R_{11}$ and $R_{12}$ together with the nitrogen to which they are bound forming heteroaryl; and wherever "heteroaryl" appears, it is a 5- or 6-membered heteroaryl optionally fused to a benzene ring; in free form or in salt form.

2. A compound according to claim 1 wherein $R_3$ is a radical of formula ($c_2$) wherein X and Y form together —CO—;

$R_{50}$ being benzyl or naphthyl-methyl wherein the phenyl or naphthyl ring is optionally substituted by OH, $C_{1-4}$alkoxy, hydroxy-$C_{1-4}$alkoxy or hydroxy-$C_{1-4}$alkyl; and $R_{51}$ being hydroxy-$C_{1-4}$alkyl; amino-$C_{1-4}$alkyl; $C_{1-4}$alkoxy-$C_{1-4}$alkyl; $C_{1-4}$alkoxy-carbonyl-$C_{1-4}$alkyl; HOOC—$C_{1-4}$alkyl; or $R_{23}R_{24}N$—CO—$C_{1-4}$alkyl wherein $R_{23}$ and $R_{24}$ are as defined in claim 2.

3. A compound according to claim 1 which is (S)-2-methyl-butyric acid (S)-(3R,7S,8aR)-8-{(S)-2-[(4R,6R)-3-(4-hydroxy-3-methoxy-benzyl)-4-methylcarbamoyl) methyl]-2-oxo-[1,3]oxazinan-6-yl]-ethyl}-3,7-dimethyl-1, 2,3,7,8,8a-hexahydro-naphthalen-1-yl ester or (S)-2-methyl-butyric acid (S)-3R,7S,8aR)-8-{(S)-2[(4-hydroxy-3-methoxy-benzyl)-4-[(2-hydroxy-ethylcarbamoyl)-methyl]-2-oxo-[1,3]oxazinan-6-yl]-ethyl-3,7-dimethyl-1,2,3,7,8,8a-hexahydro-naphthalen-1-yl ester.

4. A compound according to claim 1, in pharmaceutically acceptable salt form.

5. A pharmaceutical composition comprising a compound of formula I according to claim 1, in free form or in pharmaceutically acceptable salt form, in association with a pharmaceutically acceptable diluent or carrier therefor.

6. A method for treating myocardial infarction, stroke, gut ischemia, renal failure or hemorrhage shock in a subject in need of such treatment, which method comprises administering to said subject an effective amount of a compound of formula I according to claim 1 or a pharmaceutically acceptable salt thereof.

7. A method for treating acute or chronic rejection or organ or tissue allo- or xenograft selected from heart, lung, combined heart, lung, kidney, liver, bowel, bone marrow or pancreatic islets in a subject in need of such treatment, which method comprises administering to said subject an effective amount of a compound of formula I according to claim 1 or a pharmaceutically acceptable salt thereof.

8. A method for treating septic shock, adult respiratory distress syndrome, or traumatic shock in a subject in need of such treatment, which method comprises administering to said subject an effective amount of a compound of formula I according to claim 1 or a pharmaceutically acceptable salt thereof.

9. A method for treating rheumatoid arthritis, systemic lupus erythematosus, hashimoto's thyroidis, multiple sclerosis, myasthenia gravis, diabetes type 1 or uveitis in a subject in need of such treatment, which method comprises administering to said subject an effective amount of a compound of formula I according to claim 1 or a pharmaceutically acceptable salt thereof.

10. A method for treating psoriasis, atopic dermatitis, alopecia aerate, allergic contact dermatitis, irritant contact dermatitis, further eczematous dermatitises, seborrhoeic dermatitis, lichen planus, pemphigus, bullous pemphigoid, epidermolysis bullosa, urticaria, angloedemas, vasculitides, erythema multiforme, cutaneous eosinophilias, lupus erythematosus, acne, granuloma annulare, pyoderma gangrenosum, sun bums or toxic epidemical necrolysis in a subject in need of such treatment, which method comprises administering to said subject an effective amount of a compound of formula I according to claim 1 or a pharmaceutically acceptable salt thereof.

11. A method for treating inflammatory bowel disease in a subject in need of such treatment, which method comprises administering to said subject an effective amount of a compound of formula I according to claim 1 or a pharmaceutically acceptable salt thereof.

12. A method for treating keratoplasty, chronic keratitis, vernal conjuncitivitis or rejection of comeal transplants in a subject in need of such treatment, which method comprises administering to said subject an effective amount of a compound of formula I according to claim 1 or a pharmaceutically acceptable salt thereof.

\* \* \* \* \*

UNITED STATES PATENT AND TRADEMARK OFFICE
CERTIFICATE OF CORRECTION

PATENT NO. : 6,818,638 B2
APPLICATION NO. : 10/192888
DATED : November 16, 2004
INVENTOR(S) : Baenteli et al.

Page 1 of 1

It is certified that error appears in the above-identified patent and that said Letters Patent is hereby corrected as shown below:

On the title page

Item (63) should read:

Related U.S. Application Data

-- (63) Continuation of application No. 09/928,593, filed on August 13, 2001, now abandoned, which is a continuation of application No. PCT/EP00/01191, filed on February 14, 2000. --.

Signed and Sealed this

Second Day of January, 2007

JON W. DUDAS
*Director of the United States Patent and Trademark Office*